(12) United States Patent
Hirose et al.

(10) Patent No.: US 7,135,559 B2
(45) Date of Patent: Nov. 14, 2006

(54) PROTEINS AND NOVEL GENES ENCODING THE SAME

(75) Inventors: Kunitaka Hirose, Tokyo (JP); Jun Sakai, Tokyo (JP)

(73) Assignee: Kureha Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/220,862

(22) PCT Filed: Feb. 21, 2001

(86) PCT No.: PCT/JP01/01236

§ 371 (c)(1),
(2), (4) Date: Aug. 20, 2002

(87) PCT Pub. No.: WO01/60859

PCT Pub. Date: Aug. 23, 2001

(65) Prior Publication Data

US 2003/0049669 A1 Mar. 13, 2003

(30) Foreign Application Priority Data

Feb. 21, 2000 (JP) .................................. 2000-042933

(51) Int. Cl.
*C07H 21/02* (2006.01)

(52) U.S. Cl. ..................... 536/23.1; 435/320.1; 435/325

(58) Field of Classification Search ................. 530/350; 435/320.1, 325, 69.1, 70.1; 536/23.1
See application file for complete search history.

(56) References Cited

FOREIGN PATENT DOCUMENTS

| JP | 2001 069993 | 3/2001 |
| WO | WO 00/57903 | 10/2000 |

OTHER PUBLICATIONS

Rudinger et al. (Jun. 1976. Peptide Hormones. Biol. Council. pp. 5–7).*
Mikayama et al. (Nov. 1993. Proc.Natl.Acad.Sci. USA, vol. 90 : 10056–10060).*
Hawkins et al., Database EMBL Online, "Genomic Sequence From Human 13, Complete Sequence", retrieved from EBI Database Accession No. AC000403 XP002284062 (Apr. 9, 1997).

* cited by examiner

*Primary Examiner*—Jennifer E. Graser
(74) *Attorney, Agent, or Firm*—Darby & Darby

(57) ABSTRACT

Novel proteins, novel genes encoding the same, plasmids respectively comprising these genes, transformants respectively comprising these plasmids, antibodies or fragments thereof against the above novel proteins, methods of detecting a bacterial infection, and novel polynucleotides are disclosed. The novel proteins are activated human macrophage-specific proteins.

5 Claims, 5 Drawing Sheets

(3 of 5 Drawing Sheet(s) Filed in Color)

1 2 3 4 5 6 7 8

A  — NLG-1-1

1 2 3 4 5 6 7 8

B  — NLG-1-2

1 2 3 4 5 6 7 8

C  — NLG-2

PROTEINS AND NOVEL GENES ENCODING THE SAME

This is U.S. national phase application under 35 U.S.C. §371 of International Patent Application No. PCT/JP01/01236, filed Feb. 21, 2001. and claims the benefit of Japanese Patent Application No. 2000/42933, filed Feb. 21, 2000. The International Application was published in Japanese on Aug. 23, 2001 as WO 01/60859 under PCT Article 21(2).

TECHNICAL FIELD

The present invention relates to plural novel proteins, a novel gene encoding each of the proteins, a plasmid comprising each of the genes, a transformant comprising each of the plasmids, an antibody or a fragment thereof against each of the novel proteins, a method for detecting a bacterial infection, and novel polynucleotides. The novel proteins of the present invention are activated human macrophage-specific proteins.

BACKGROUND ART

It is known that a Lipopolysaccharide (LPS) is a glycolipid existing in an outer membrane of Gram-negative bacterium and activates a macrophage to induce an expression of many genes. Known examples of such genes having expressions that are induced by the LPS are those of interleukin (IL)-1, exhibiting an antitumor function or an inflammatory function, such as a function to cause an inflammation by a bacterial infection, IL-6, IL-12, IL-15, IL-18, a tumor necrosis factor (TNF), or a chemokine (such as IL-8 or MCP); granulocyte colony-stimulating factor (G-CSF) exhibiting a hemapoietic function, monocyte (M)-CSF, or GM-CSF; or collagenase playing a main role in an inflammation such as that caused by a bacterial infection, cyclooxygenase (COX), or a nitrogen oxide synthase (iNOS) or the like. Almost all of the above proteins encoded by the above genes are physiologically active proteins playing important roles in a body [Annu. Rev. lmmunol., 2, 283–318 (1984); Inflammation: Basic Principles and Clinical Correlates, 637–662, Raven Press Ltd., New York (1992)].

There are about 0.1 million genes in the human chromosome, but only 10 or 20 percentage thereof have been isolated and identified. Therefore, as almost all of the genes have not been isolated or analyzed, it is believed that almost all of the genes having an expression that is specifically induced by LPS are unidentified novel genes.

Septicemia is a systemic disease wherein a festering lesion exists in a body, and many bacteria are intermittently or continuously introduced into the blood from the festering lesion. A diagnosis of the septicemia is carried out by culturing the blood, and when the existence of bacteria is proved, the illness is definitely diagnosed as the septicemia. However, the above method has disadvantages, namely, the method is time-consuming, and when a blood sample is drawn, it may be contaminated with bacteria from skin, such as *Staphylococcus epidermidis*.

Therefore, the inventors of the present invention made an intensive search for genes having an expression that is induced specifically at a macrophage by an LPS-stimulation, for the purpose of an application for developing a new method of diagnosis and/or medicament for treating a disease such as inflammation, allergy, or cancer, particularly a bacterial infection. As a result, three novel genes were isolated and identified. Further, the present inventors found that these three genes were not expressed in healthy persons, but were expressed in patients suffering from a bacterial infection. The invention is based on the above findings.

DISCLOSURE OF INVENTION

The present invention relates to
(1) a protein comprising an amino acid sequence of SEQ ID NO: 2 in the sequence listing, or a variation functionally equivalent thereto, or a fragment of the protein or the variation (hereinafter sometimes collectively referred to as a "first novel protein of the present invention"),
(2) a protein comprising an amino acid sequence of SEQ ID NO: 4 in the sequence listing, or a variation functionally equivalent thereto, or a fragment of the protein or the variation (hereinafter sometimes collectively referred to as a "second novel protein of the present invention"), and
(3) a protein comprising an amino acid sequence of SEQ ID NO: 6 in the sequence listing, or a variation functionally equivalent thereto, or a fragment of the protein or the variation (hereinafter sometimes collectively referred to as a "third novel protein of the present invention").

Further, the present invention relates to
(1) a gene encoding the above-mentioned "first novel protein of the present invention" (hereinafter sometimes referred to as a "first novel gene of the present invention"),
(2) a gene encoding the above-mentioned "second novel protein of the present invention" (hereinafter sometimes referred to as a "second novel gene of the present invention"), and
(3) a gene encoding the above-mentioned "third novel protein of the present invention" (hereinafter sometimes referred to as a "third novel gene of the present invention").

Further, the present invention relates to plasmids comprising each of the above-mentioned genes.

Further, the present invention relates to transformants comprising each of the above-mentioned plasmids.

Further, the present invention relates to antibodies or fragments thereof, characterized by being reactive specifically to each of the above-mentioned proteins or variations functionally equivalent thereto.

Further, the present invention relates to a method for detecting a bacterial infection, characterized by analyzing the proteins or the variations functionally equivalent thereto, or the mRNAs thereof, in a sample to be detected.

Further, the present invention relates to
(1) a polynucleotide capable of specifically hybridizing to an mRNA consisting of an base sequence of SEQ ID NO: 1 in the sequence listing (hereinafter sometimes referred to as a "first probe of the present invention"),
(2) a polynucleotide capable of specifically hybridizing to an mRNA consisting of an base sequence of SEQ ID NO: 3 in the sequence listing (hereinafter sometimes referred to as a "second probe of the present invention"), and
(3) a polynucleotide capable of specifically hybridizing to an mRNA consisting of an base sequence of SEQ ID NO: 5 in the sequence listing (hereinafter sometimes referred to as a "third probe of the present invention").

The term "variation functionally equivalent" as used herein means a protein having an amino acid sequence wherein one or more (particularly one or several) amino acids are deleted in, changed in, or added to the amino acid sequence of an original protein, and exhibiting the same activities as the original protein. The term "added" as used herein includes an addition of one or more (particularly one or several) amino acids to an N-terminus and/or a C-terminus of an amino acid sequence, and an insertion of one or more (particularly one or several) amino acids to an inside of an amino acid sequence.

Further, the term "homologous protein" as used herein means a protein comprising an amino acid sequence having a 90% or more (preferably 95% or more, more preferably 98% or more, most preferably 99% or more) homology with the amino acid sequence of an original protein, and exhibiting the same activities as the original protein. The term "homology" as used herein means a value calculated by BLAST [Basic local alignment search tool; Altschul, S. F. et al., J. Mol. Biol., 215, 403–410, (1990)].

Furthermore, the terms "gene" and "polynucleotide" as used herein include both of DNA and RNA.

BRIEF DESCRIPTION OF DRAWINGS

The patent or application file contains at least one drawing executed in color. Copies of this patent or patent application publication with color drawings(s) will be provided by the Office upon request and payment of the necessary fee.

BEST MODE FOR CARRYING OUT THE INVENTION

Figure 1:
FIG. 1 shows the results of electrophoresis wherein the expression of three novel genes of the present invention in human macrophages stimulated by LPS or not stimulated by LPS was detected by a northern blotting method.

The present invention will be explained in detail hereinafter.

The first novel protein of the present invention includes (1) a protein comprising an amino acid sequence of SEQ ID NO: 2 in the sequence listing,
(2) a variation functionally equivalent to the protein (1),
(3) a protein homologous to the protein (1), and
(4) a fragment thereof [i.e., a fragment of the protein (1), the variation (2), or the homologous protein (3)]. A protein consisting of the amino acid sequence of SEQ ID NO: 2 in the sequence listing, or a variation functionally equivalent or protein homologous thereto are preferred.

The protein consisting of the amino acid sequence of SEQ ID NO: 2 in the sequence listing consists of 481 amino acid residues. The protein consisting of the amino acid sequence of SEQ ID NO: 2 in the sequence listing has a high homology of approximately 82% in the amino acid sequence with mouse IRG-1 (lmmune-responsive protein-1) [Immnogenetics, 41, 263–270, (1995)], and thus seems to be human IRG-1.

In the amino acid sequence of SEQ ID NO: 2 in the sequence listing, there exist eight known sites to be phospholylated by protein kinase C and ten known sites to be phospholylated by casein kinase C. As a result, it is believed that the protein consisting of the amino acid sequence of SEQ ID NO: 2 in the sequence listing plays an important role in an intracellular signal transduction system which transduces information of LPS-stimulation.

Further, a signal peptide sequence at the N-terminus does not exist, and thus, it is believed that the protein consisting of the amino acid sequence of SEQ ID NO: 2 in the sequence listing exhibits biological activities in cells.

As the protein comprising the amino acid sequence of SEQ ID NO: 2 in the sequence listing, there may be mentioned, for example, a fusion protein of the protein consisting of the amino acid sequence of SEQ ID NO: 2 in the sequence listing with a fusion partner. In the fusion protein, the fusion partner may be linked with the N-terminus and/or C terminus of the protein consisting of the amino acid sequence of SEQ ID NO: 2.

As the fusion partner, for example, a protein for purification such as the whole or a part of glutathione-S-transferase (GST), a protein for detection such as the whole or a part of β-galactosidase α peptide (LacZ α), or a protein for expression such as a signal sequence may be used.

Further, in the fusion protein, an amino acid sequence which may be restrictively digested with a proteolytic enzyme such as thrombin or factor Xa may be optionally inserted between the protein consisting of the amino acid sequence of SEQ ID NO: 2 in the sequence listing and the fusion partner.

The fragment of the protein comprising the amino acid sequence of SEQ ID NO: 2 in the sequence listing or the variation functionally equivalent or protein homologous thereto is not particularly limited, so long as it may be used as an immunogen to prepare the first antibody or fragment thereof according to the present invention, but preferably consists of 13 or more amino acid residues, more preferably 20 or more amino acid residues, most preferably 50 or more amino acid residues.

The first novel protein of the present invention may be obtained by various known methods. For example, the protein may be prepared by using a known genetic engineering technique and the first novel gene of the present invention.

The first novel gene of the present invention is not particularly limited, so long as it encodes the first novel protein of the present invention. As the gene, there may be mentioned, for example, a gene consisting of the 37th to 1479th bases in the base sequence of SEQ ID NO: 1 in the sequence listing.

The gene consisting of the 37th to 1479th bases in the base sequence of SEQ ID NO: 1 in the sequence listing encodes the protein consisting of the amino acid sequence of SEQ ID NO: 2 in the sequence listing. Further, the gene consisting of the 37th to 1479th bases in the base sequence of SEQ ID NO: 1 in the sequence listing is not expressed in healthy persons, but is expressed in patients suffering from a bacterial infection.

The first probe of the present invention is not particularly limited, so long as it is capable of specifically hybridizing to an mRNA consisting of the base sequence of SEQ ID NO: 1 in the sequence listing. As the probe, there may be mentioned, for example, a single or double stranded polynucleotide consisting of a base sequence complementary to that of SEQ ID NO: 1 in the sequence listing, or a partial base sequence thereof. The lower limit of the number of bases in the first probe of the present invention is not particularly limited, but is preferably 18 or more, more particularly 26 or more, most particularly 41 or more. Further, the upper limit thereof is not particularly limited, but is preferably 2180 or less. The expression "specifically hybridize with an mRNA consisting of the base sequence of SEQ ID NO: 1 in the sequence listing" as used herein means that a polynucleotide does not hybridize with mRNAs derived from a healthy person, but will hybridize with the mRNA consisting of the base sequence of SEQ ID NO: 1 in the sequence listing, under the conditions described in Example 1(4). In those conditions, it is twice washed with 2×SSC (standard sodium citrate) containing 0.1% sodium dodecyl sulfate (SDS) at room temperature for 20 minutes, and further twice washed with 0.2×SSC containing 0.1% SDS at 65° C. for 20 minutes.

The second novel protein of the present invention includes
(1) a protein comprising an amino acid sequence of SEQ ID NO: 4 in the sequence listing,
(2) a variation functionally equivalent to the protein (1),
(3) a protein homologous to the protein (1), and
(4) a fragment thereof [i.e., a fragment of the protein (1), the variation (2), or the homologous protein (3)]. A protein consisting of the amino acid sequence of SEQ ID NO: 4 in the sequence listing, or a variation functionally equivalent or protein homologous thereto are preferred.

The protein consisting of the amino acid sequence of SEQ ID NO: 4 in the sequence listing consists of 390 amino acid residues. The protein consisting of the amino acid sequence of SEQ ID NO: 4 in the sequence listing has a high homology of approximately 82% in the amino acid sequence with mouse IRG-1 (1mmune-responsive protein-1) [*Immnogenetics*, 41, 263–270, (1995)], and thus seems to be human IRG-1.

In the amino acid sequence of SEQ ID NO: 4 in the sequence listing, there exist six known sites to be phospholylated by protein kinase C and eight known sites to be phospholylated by casein kinase C. As a result, it is believed that the protein consisting of the amino acid sequence of SEQ ID NO: 4 in the sequence listing plays an important role in an intracellular signal transduction system which transduces information of LPS-stimulation.

Further, a signal peptide sequence at the N-terminus does not exist, and thus, it is believed that the protein consisting of the amino acid sequence of SEQ ID NO: 4 in the sequence listing exhibits biological activities in cells.

As the protein comprising the amino acid sequence of SEQ ID NO: 4 in the sequence listing, there may be mentioned, for example, a fusion protein of the protein consisting of the amino acid sequence of SEQ ID NO: 4 in the sequence listing with a fusion partner. In the fusion protein, the fusion partner may be linked with the N-terminus and/or C terminus of the protein consisting of the amino acid sequence of SEQ ID NO: 4.

As the fusion partner, for example, a protein for purification such as the whole or a part of glutathione-S-transferase (GST), a protein for detection such as the whole or a part of β-galactosidase α peptide (LacZ α), or a protein for expression such as a signal sequence may be used.

Further, in the fusion protein, an amino acid sequence which may be restrictively digested with a proteolytic enzyme such as thrombin or factor Xa may be optionally inserted between the protein consisting of the amino acid sequence of SEQ ID NO: 4 in the sequence listing and the fusion partner.

The fragment of the protein comprising the amino acid sequence of SEQ ID NO: 4 in the sequence listing or the variation functionally equivalent or protein homologous thereto is not particularly limited, so long as it may be used as an immunogen to prepare the second antibody or fragment thereof according to the present invention, but preferably consists of 13 or more amino acid residues, more preferably 20 or more amino acid residues, most preferably 50 or more amino acid residues.

The second novel protein of the present invention may be obtained by various known methods. For example, the protein may be prepared by using a known genetic engineering technique and the second novel gene of the present invention.

The second novel gene of the present invention is not particularly limited, so long as it encodes the second novel protein of the present invention. As the gene, there may be mentioned, for example, a gene consisting of the 126th to 1295th bases in the base sequence of SEQ ID NO: 3 in the sequence listing.

The gene consisting of the 126th to 1295th bases in the base sequence of SEQ ID NO: 3 in the sequence listing encodes the protein consisting of the amino acid sequence of SEQ ID NO: 4 in the sequence listing. Further, the gene consisting of the 126th to 1295th bases in the base sequence of SEQ ID NO: 3 in the sequence listing is not expressed in healthy persons, but is expressed in patients suffering from a bacterial infection.

The second probe of the present invention is not particularly limited, so long as it is capable of specifically hybridizing to an mRNA consisting of the base sequence of SEQ ID NO: 3 in the sequence listing. As the probe, there may be mentioned, for example, a single or double stranded polynucleotide consisting of a base sequence complementary to that of SEQ ID NO: 3 in the sequence listing, or a partial base sequence thereof. The lower limit of the number of bases in the second probe of the present invention is not particularly limited, but is preferably 18 or more, more particularly 26 or more, most particularly 41 or more. Further, the upper limit thereof is not particularly limited, but is preferably 1970 or less. The expression "specifically hybridize with an mRNA consisting of the base sequence of SEQ ID NO: 3 in the sequence listing" as used herein means that a polynucleotide does not hybridize with mRNAs derived from a healthy person, but will hybridize with the mRNA consisting of the base sequence of SEQ ID NO: 3 in the sequence listing, under the conditions described in Example 1(4).

The third novel protein of the present invention includes
(1) a protein comprising an amino acid sequence of SEQ ID NO: 6 in the sequence listing,
(2) a variation functionally equivalent to the protein (1),
(3) a protein homologous to the protein (1), and
(4) a fragment thereof [i.e., a fragment of the protein (1), the variation (2), or the homologous protein (3)]. A protein consisting of the amino acid sequence of SEQ ID NO: 6 in the sequence listing, or a variation functionally equivalent or protein homologous thereto are preferred.

The protein consisting of the amino acid sequence of SEQ ID NO: 6 in the sequence listing consists of 83 amino acid residues. The protein consisting of the amino acid sequence of SEQ ID NO: 6 in the sequence listing has a homology of approximately 27% in the amino acid sequence with mouse NADH-ubiquinoneoxidoreductase MLRQ subunit (CI-MLRQ). It is reported that the mouse NADH-ubiquinoneoxidoreductase MLRQ subunit exists in the complex I, one of four complexes I, II, III, and IV which form an electron transport system of a mitochondrion, and takes part in a production of an active oxygen [Circulation Res., 85, 357–363 (1999); Biochem. Mol. Biol. Int., 43, 669–675 (1997)]. The protein consisting of the amino acid sequence of SEQ ID NO: 6 in the sequence listing does not have a gap, as suggested from the amino acid sequence thereof, and it is assumed that the protein has a structure similar to that of the mouse NADH-ubiquinoneoxidoreductase MLRQ subunit. Therefore, the protein may contain an electron transport activity and take part in a production of an active oxygen upon inflammation.

Further, a signal peptide sequence at the N-terminus does not exist, and thus, it is believed that the protein consisting of the amino acid sequence of SEQ ID NO: 6 in the sequence listing exhibits biological activities in cells.

As the protein comprising the amino acid sequence of SEQ ID NO: 6 in the sequence listing, there may be mentioned, for example, a fusion protein of the protein consisting of the amino acid sequence of SEQ ID NO: 6 in the sequence listing with a fusion partner. In the fusion protein, the fusion partner may be linked with the N-terminus and/or C terminus of the protein consisting of the amino acid sequence of SEQ ID NO: 6.

As the fusion partner, for example, a protein for purification such as the whole or a part of glutathione-S-transferase (GST), a protein for detection such as the whole or a part of β-galactosidase α peptide (LacZ α), or a protein for expression such as a signal sequence may be used.

Further, in the fusion protein, an amino acid sequence which may be restrictively digested with a proteolytic enzyme such as thrombin or factor Xa may be optionally inserted between the protein consisting of the amino acid sequence of SEQ ID NO: 6 in the sequence listing and the fusion partner.

The fragment of the protein comprising the amino acid sequence of SEQ ID NO: 6 in the sequence listing or the variation functionally equivalent or protein homologous thereto is not particularly limited, so long as it may be used as an immunogen to prepare the third antibody or fragment thereof according to the present invention, but preferably consists of 13 or more amino acid residues, more preferably 20 or more amino acid residues, most preferably 50 or more amino acid residues.

The third novel protein of the present invention may be obtained by various known methods. For example, the protein may be prepared by using a known genetic engineering technique and the third novel gene of the present invention.

The third novel gene of the present invention is not particularly limited, so long as it encodes the third novel protein of the present invention. As the gene, there may be mentioned, for example, a gene consisting of the 56th to 304th bases in the base sequence of SEQ ID NO: 5 in the sequence listing.

The gene consisting of the 56$^{th}$ to 304$^{th}$ bases in the base sequence of SEQ ID NO: 5 in the sequence listing encodes the protein consisting of the amino acid sequence of SEQ ID NO: 6 in the sequence listing. Further, the gene consisting of the 56$^{th}$ to 304$^{th}$ bases in the base sequence of SEQ ID NO: 5 in the sequence listing is not expressed in healthy persons, but is expressed in patients suffering from a bacterial infection.

The third probe of the present invention is not particularly limited, so long as it is capable of specifically hybridizing to an mRNA consisting of the base sequence of SEQ ID NO: 5 in the sequencing listing. As the probe, there may be mentioned, for example, a single or double stranded polynucleotide consisting of a base sequence complementary to that of SEQ ID NO: 5 in the sequence listing, or a partial base sequence thereof. The lower limit of the number of bases in the third probe of the present invention is not particularly limited, but is preferably 18 or more, more particularly 26 or more, most particularly 41 or more. Further, the upper limit thereof is not particularly limited, but is preferably 652 or less. The expression "specifically hybridize with an mRNA consisting of the base sequence of SEQ ID NO: 5 in the sequence listing" as used herein means that a polynucleotide does not hybridize with mRNAs derived from a healthy person, but will hybridize with the mRNA consisting of the base sequence of SEQ ID NO: 5 in the sequence listing, under the conditions described in Example 1 (4).

The plasmid of the present invention is not particularly limited, so long as it comprises the novel gene of the present invention, i.e., the first novel gene of the present invention, the second novel gene of the present invention, or the third novel gene of the present invention. For example, it may be a respective plasmid prepared by incorporating each of the above genes of the present invention into a known vector suitably selected depending on a host cell used, that is, the first plasmid of the present invention comprising the first novel gene of the present invention, the second plasmid of the present invention comprising the second novel gene of the present invention, and the third plasmid of the present invention comprising the third novel gene of the present invention.

The transformant of the present invention is not particularly limited, so long as it comprises the plasmid of the present invention, i.e., the first plasmid of the present invention, the second plasmid of the present invention, or the third plasmid of the present invention. For example, it may be a transformant prepared by transforming a desired host cell with each of the plasmids of the present invention, that is, the first transformant comprising the first plasmid of the present invention, the second transformant comprising the second plasmid of the present invention, or the third transformant comprising the third plasmid of the present invention.

The host cell may be, for example, a known microorganism usually used, for example, *E. coli* or *Saccharomyces cerevisiae,* or a known cultivated cell, such as an animal cell, such as a CHO cell or a COS cell, or an insect cell such as a BmN4 cell.

The known expression vector may be, for example, pUC, pTV, PGEX, pKK, or pTrcHis for *E. coli;* pEMBLY or pYES2 for a yeast; pMAMneo for a CHO cell; pcDNA3 for a COS cell; a vector (such as pBK283) containing a polyhedrin promoter of a silkworm nucleopolyhederovirus (BmNPV).

The first antibody of the present invention or the fragment thereof is reacted specifically with the first protein of the present invention or the variation functionally equivalent thereto, respectively. The second antibody of the present invention or the fragment thereof is reacted specifically with the second protein of the present invention or the variation functionally equivalent thereto, respectively. The third antibody of the present invention or the fragment thereof is reacted specifically with the third protein of the present invention or the variation functionally equivalent thereto, respectively.

The antibody of the present invention may be a monoclonal antibody or a polyclonal antibody.

The respective monoclonal antibodies of the present invention, that is, the first monoclonal antibody of the present invention specifically reactive with the first protein or the variation functionally equivalent thereto of the present invention, respectively, the second monoclonal antibody of the present invention specifically reactive with the second protein or the variation functionally equivalent thereto of the present invention, respectively, or the third monoclonal antibody of the present invention specifically reactive with the third protein or the variation functionally equivalent thereto of the present invention, respectively, may be prepared by a method which is in itself known, except that the novel protein of the present invention, the variation functionally equivalent thereto, or a fragment thereof is used as an immunogen or an antigen for a screening.

For example, a hybridoma secreting the monoclonal antibody of the present invention may be prepared by immunizing a mouse with the above immunogen, fusing a splenic cell taken from the immunized mouse and a mouse myeloma cell in accordance with a cell-fusion method disclosed in Nature, 256, 495 (1975), or an electric cell-fusion method disclosed in J. Immunol. Method, 100, 181–189 (1987), and carrying out a screening with the antigen for a screening as above.

As the medium for cultivating the hybridomas, any medium suitable for a cultivation of a hybridoma may be used. Preferably, the Dulbecco's modified Eeagle's minimum essential medium containing fetal calf serum, L-glutamine, L-pyruvic acid, and antibiotics (penicillin G and streptomycin) may be used.

The cultivation of the hybridoma may be carried out in 5% $CO_2$ and at 37° C. for about 3 days in a medium, or for about 14 days in the abdominal cavities of mice.

It is possible to isolate or purify the monoclonal antibody from the resulting culture liquid or mouse ascites, using a method generally applied for the isolation and purification of proteins.

As examples thereof, there may be mentioned ammonium sulfate salting out, ion exchange column chromatography using ion exchange cellulose, molecular sieve column chromatography using molecular sieve gel, affinity column chromatography using protein A binding polysaccharides, dialysis, lyophilization, or the like.

The respective polyclonal antibodies of the present invention, that is, the first polyclonal antibody of the present invention specifically reactive with the first protein or the variation functionally equivalent thereto of the present invention, respectively, the second polyclonal antibody of the present invention specifically reactive with the second protein or the variation functionally equivalent thereto of the present invention, respectively, or the third polyclonal antibody of the present invention specifically reactive with the third protein or the variation functionally equivalent thereto of the present invention, respectively, may be also prepared by a method which is in itself known, except that the novel protein of the present invention, the variation functionally equivalent thereto, or a fragment thereof is used as an immunogen or an antigen for a screening by, for example, the following method.

That is, a physiological salt solution containing an antigen is mixed with an equal volume of complete Freund's adjuvant or incomplete adjuvant, or an equivalent thereof, such as Hunter's TiterMax™ (Funakoshi; Cat. No. YT001-00, Tokyo, Japan), until emulsified. The resulting emulsion is administered subcutaneously, intraperitoneally, or intramuscularly to a mammal, for example, a rabbit or goat (a first immunization). Then, the same procedure is repeated at intervals of two to four weeks for several immunizations. One or two weeks after a final immunization, blood is taken from a carotid artery or a heart of the mammal, and salted-out with ammonium sulfate to prepare a serum.

Each of the antibody-fragments of the present invention is not particularly limited, so long as it is a partial fragment of the antibody (including the monoclonal antibody and the polyclonal antibody) of the present invention, and has a specific reactivity that is the same as that of the original antibody. The fragment of the present invention may be, for example, Fab, Fab', F(ab')$_2$, or Fv. The antibody fragment of the present invention may be prepared, for example, by digesting the polyclonal antibody or monoclonal antibody of the present invention with a known protease by a conventional method, and then isolating and purifying by a conventional method.

The inventors of the present invention found that the protein of the present invention, particularly, the protein consisting of the amino acid sequence of SEQ ID NO: 2 in the sequence listing, the protein consisting of the amino acid sequence of SEQ ID NO: 4 in the sequence listing, or the protein consisting of the amino acid sequence of SEQ ID NO: 6 in the sequence listing, and the mRNA thereof, is not expressed in a healthy person but in a patient suffering from a bacterial infection, such as septicemia, pneumonia, urinary tract infection, myelitis, or tympanitis. Therefore, the proteins of the present invention or mRNAs thereof may be used as a diagnostic marker of a patient suffering from a bacterial infection. More particularly, when an in vitro detection method of the present invention finds an existence of the protein of the present invention and/or mRNA thereof in a sample taken from a subject, the subject can be judged to be a patient suffering from a bacterial infection. On the contrary, when the protein and/or the mRNA is not found, the subject can be judged to be a person not suffering from a bacterial infection.

The sample which may be used in the present invention is not particularly limited, so long as it has a possibility of including the protein of the present invention and/or the mRNA thereof. The sample may be a biological sample taken from an animal, such as a mammal, particularly a human (particularly a patient), for example, a tissue (e.g., cells) or an extract therefrom, blood such as serum or plasma, urine, or a humor such as cerebrospinal fluid. A sample used in a conventional clinical examination may be used in the present invention without limitation.

The method of the present invention will be explained hereinafter with respect to the method for detecting a bacterial infection by analyzing the mRNA of the protein of the present invention, and then, with respect to the method for detecting a bacterial infection by analyzing the protein of the present invention.

In the methods of the present invention, the method for detecting a bacterial infection by analyzing the mRNA of the protein of the present invention is not particularly limited but, for example, may be a method comprising steps of bring a sample into contact with a polynucleotide comprising a base sequence complementary to the base sequence of the mRNA of the protein of the present invention; and analyzing a coupled product of the polynucleotide and the mRNA of the protein of the present invention (hereinafter referred to as a "first detecting method of the present invention"), or a method comprising the steps of reverse-transcribing an mRNA in a sample to a cDNA, amplifying genes in accordance with a gene-amplifying reaction, particularly, a polymerase chain reaction (PCR), using a reaction product obtained in the reverse-transcribing step, and primers which may amplify genes with the gene encoding the present protein as a template, and analyzing the amplified genes in the above gene-amplifying step (hereinafter referred to as a "second detecting method of the present invention").

In the first method for detection of the present invention, the sample is reacted with a polynucleotide (for example, the probe of the present invention) comprising a base sequence complementary to that of the mRNA of the protein of the present invention, and the resulting complex of the polynucleotide and "the mRNA of the protein of the present invention" is detected, or the amount of the complex is measured to thereby analyze the mRNA of the protein of the present invention.

The polynucleotide comprises a sequence complementary or substantially complementary to that of a part of the mRNA transcribed from a selected gene (DNA), and thus forms a double strand with the mRNA transcribed from the target gene. It is believed that any polynucleotide sufficiently complementary to form a stable complex with a target mRNA can be used. The polynucleotide able to be used in the present invention may be complementary to substantially any region in a target mRNA. The polynucleotide can be used as a DNA probe for detecting an increase or a decrease of an expression of the mRNA specific to the gene of the protein according to the present invention. That is, the polynucleotide is specifically attached to the mRNA of the protein according to the present invention as a target, and forms a molecular hybrid, whereby a degree of expression of the mRNA of the protein according to the present invention in cells can be detected.

The polynucleotide able to be used in the first method for detection of the present invention may be prepared by appropriately selecting a base sequence complementary to a specific base sequence of the mRNA of the protein according to the present invention, and using a known DNA synthesizer, a PCR apparatus, a gene cloning or the like. Various length polynucleotides may be used, but the polynucleotide preferably has 10 or more bases, more preferably 17 or more bases.

The polynucleotide may be a non-modified polynucleotide or a polynucleotide analogue. An appropriate analogue may be, for example, an ethyl or methyl phosphate analogue, or a phosphorothioated polydeoxynucleotide [Nucleic Acids Res., 14, 9081–9093, (1986); J. Am. Chem. Soc., 106, 6077–6079, (1984)], with recent improvement in the production of polynucleotide analogue, for example, a 2'-O-methylribonucleotide [Nucleic Acids Res., 15, 6131–6148, (1987)], or a conjugated RNA-DNA analogue, i.e., chimera polynucleotide [FEBS Lett., 215, 327–330, (1987)], may be used.

The selected polynucleotide may be of any kind, for example, may have an electrical charge or no electrical charge. The polynucleotide may be labeled with a known labeling agent, such as a radioactive isotope, or a fluorescent substance by a conventional method, so as to carry out the above experiment in vitro or in vivo. The radioactive isotope may be, for example, $^{125}I$, $^{131}I$, $^3H$, $^{14}C$, $^{32}P$, or $^{35}S$. Of these radioactive isotopes, it is preferable to label the polynucleotide with $^{32}P$ by a random primer method [Anal. Biochem., 132, 6–13, (1983)]. Further, a fluorescent coloring agent forming a derivative may be used as a labeling agent, as this enables an easy handling with a low risk factor. As the fluorescent coloring agent, any coloring agents capable of binding the polynucleotide may be used. For example, fluorescein, rhodamin, Texas red, 4-fluoro-7-nitrobenzofurazane (NBD), coumarin, fluorescamine, succinyl fluorescein, or dansyl may be preferably used.

An amount of an mRNA of the protein according to the present invention may be measured by a northern blotting method, using cDNA of the protein according to the present invention as follows: an mRNA is extracted and isolated from any somatic cell or tissue, then the isolated mRNA is electrophoresed on an agarose gel and transferred onto a nitro cellulose or nylon membrane, and then reacted with a cDNA probe of the protein according to the present invention to measure an amount of the mRNA of the protein according to the present invention. The cDNA probe of the protein according to the present invention as used is a DNA complementary to the mRNA of the protein according to the present invention, and has preferably 17 or more bases.

In the reverse-transcribing step and the gene-amplifying step (particularly, the PCR step) of the second detecting method according to the present invention, the reactions per se may be carried out in accordance with the conventional reverse-transcribing method and the conventional gene-amplifying method, for example, a reverse-transcription PCR (RT-PCR). More particularly, a reverse-transcriptase and oligo(dT) primers are used to carry out the reverse-transcription. Then, a thermostable DNA polymerase, such as a Taq polymerase, is used to carry out an initial denaturing reaction, for example at 97° C. for 2 to 3 minutes. Subsequently, an amplifying cycle consisting of (1) a step for denaturing DNAs at 90 to 94° C. for 30 seconds, (2) a step for annealing single-strand DNAs and primers at 50 to 55° C. for 30 seconds, and (3) a step for synthesizing DNAs by the thermostable DNA polymerase at 70 to 75° C. for 1 to 2 minutes is repeated, for example 15 to 45 times, to perform the PCR.

The analyzing step of the second detecting method according to the present invention can be carried out in accordance with, for example, a conventional analyzing method, for example, a method comprising steps of carrying out agarose-gel electrophoresis and then staining the gel with a suitable DNA-binding colorant such as ethidium bromide, or a southern blotting, or the like The method for detecting a bacterial infection by analyzing the protein of the present invention, one of the methods according to the present invention, is not particularly limited but, for example, may comprise steps of bringing a sample into contact with an immunoreactive substance which can immunologically react with the protein of the present invention, and analyzing a coupled product of the immunoreactive substance and the protein of the present invention (hereinafter referred to as a "third detecting method of the present invention").

In the third detecting method of the present invention, the sample is brought into contact with the immunoreactive substance which may immunologically react with the protein of the present invention. When a sample from a human is used, the sample is preferably brought into contact with an immunoreactive substance which can immunologically react with the protein consisting of the amino acid sequence of SEQ ID NO: 2, the protein consisting of the amino acid sequence of SEQ ID NO: 4, or the protein consisting of the amino acid sequence of SEQ ID NO: 6.

When the sample is brought into contact with the substance immunologically reactive to the protein of the present invention, if the sample does not contain the protein of the present invention, a reaction with the immunologically reactive substance does not occur. If the sample contains the protein of the present invention, the immunologically reactive substance binds the protein of the present invention, and a complex of the immunologically reactive substance and the protein of the present invention is formed in an amount correlated with that of the protein of the present invention present in the sample. The complex may be easily detected by a known method, and therefore, an existence of the protein of the present invention in the sample can be detected by detecting the existence of the complex, or an amount of the protein of the present invention in the sample can be measured by measuring the amount of the complex.

The protein of the present invention in a tissue or a cell may be measured by using a tissue section sample or a cell sample in a fluorescent antibody technique or an enzyme antibody technique.

The immunologically reactive substance capable of immunologically reacting the protein of the present invention includes an antiserum against the protein of the present invention, a polyclonal antibody against the protein of the present invention, or a monoclonal antibody against the protein of the present invention, or a fragment of these antibodies. The immunologically reactive substance may be used singly or in a combination thereof. The fragment includes, for example, Fab, Fab', F(ab')$_2$, or Fv.

In the third method for detection according to the present invention, the sample is brought into contact with the immunologically reactive substance capable of immunologically reacting the protein of the present invention, and a complex of the protein in the present invention and the immunologically reactive substance is formed. Then, the protein in the present invention bound to the antibody is detected and the amount thereof is measured by an immunochemical method, to thereby find a level of the protein of the present invention in the sample.

Principally, the immunochemical method may be, for example, any conventional immunoassay, for example, EIA, ELISA, RIA or the like. The immunochemical methods are generally classified as follows:

(1) Competitive Assay:

A sample containing an unknown amount of antigens and a given amount of labeled antigens is competitively reacted with a given amount of antibodies, and then an activity of the labeled antigens bound to the antibodies or an activity of the labeled antigens not bound to the antibodies is measured.

(2) Sandwich Assay:

An excess amount of antibodies immobilized on carriers is added and reacted to a sample containing an unknown amount of antigens (a first reaction). Then, a given excess amount of labeled antibodies is added and reacted therewith (a second reaction). An activity of the labeled antibodies on the carriers is measured. Alternatively, an activity of the labeled antibodies which are not on the carriers is measured. The first reaction and the second reaction may be carried out at the same time, or sequentially.

When a labeling agent is a radioactive isotope, a well counter or a scintillation counter may be used for measurement. When the labeling agent is an enzyme, an enzymatic activity can be measured by colorimetry or fluorimetry, after adding a substrate and allowing to stand. When the labeling agent is a fluorescent substance or an luminescent substance, a known method therefor may be used, respectively.

Recently, in addition to the above methods, a western blotting method has been used wherein electrophoresed proteins are transferred onto a filter such as a nitrocellulose membrane, and a target protein is detected with an antibody. The western blotting method may also be used in the detection of the protein according to the present invention.

The antibody used in the above methods can be labeled with an appropriate marker. Examples are a radioactive isotope, an enzyme, a fluorescent substance, or a luminescent substance, by a known method of labeling antibodies.

The radioactive isotope may be, for example, $^{125}$I, $^{131}$I, $^{3}$H, $^{14}$C, or $^{35}$S.

Preferably, the enzyme used is stable and has a large specific activity. Examples of the enzyme are a glycosidase (such as, β-galactosidase, β-glucosidase, β-glucuronidase, β-fructosidase, α-galactosidase, α-glucosidase, or α-mannosidase), an amylase (such as, α-amylase, β-amylase, isoamylase, glucoamylase, or taka-amylase), a cellulase, or a carbohydrase such as lysozyme; a urease, or an amidase such as asparaginase; a choline esterase, such as acetylcholinesterase, a phosphatase, such as alkaline phosphatase, a sulfatase, an esterase such as lipase; a nuclease such as deoxyribonuclease or ribonuclease; an iron porphyrin enzyme, such as a catalase, peroxidase or cytochrome oxidase; a copper enzyme, such as a tyrosinase or ascorbate oxidase; dehydrogenase, such as an alcohol dehydrogenase, malate dehydrogenase, lactate dehydrogenase, or isocitrate dehydrogenase.

The fluorescent substance may be, for example, fluorescamine, or a fluorescence isothiocyanate, and the luminescent substance may be, for example, luminol, a luminol derivative, luciferin or lucigenin. A signal from the above label may be detected by known methods.

The labeling agent can be bound to antibodies by any conventional method, such as a chloramin T method [Nature, 194, 495–496, (1962)], a periodic acid method [Journal of Histochemistry and Cytochemistry, 22, 1084–1091, (1974)], or a maleimide method [Journal of Biochemistry, 79, 233–236, (1976)].

An EIA method, as one of the above measurement methods will be mentioned hereinafter. A sample is added to the first antibodies immobilized on a carrier (such as an assay plate), and the first antibodies are bound to the proteins of the present invention to form complexes. To the complexes, the second antibodies labeled with enzyme (such as peroxidase) are added to react with the complexes to form "first antibody/protein of the present invention/second antibody" complexes. To the resulting "first antibody/protein of the present invention/second antibody" complexes, a substrate for the enzyme label (such as peroxidase) is added, and an absorbance or fluorescent strength of products of the enzymatic reaction is measured, whereby enzymatic activities of the enzyme labels attached to the "first antibody/protein in the present invention/second antibody" complexes are measured. A series of the above procedures is carried out in advance for a standard solution containing a known amount of the protein of the present invention, and a standard curve based on the relationship between the protein of the present invention and the absorbance or fluorescent strength is prepared. A comparison is made between the standard curve and absorbance or fluorescent strength for a sample containing an unknown amount of the proteins according to the present invention, and thus, the amount of the proteins according to the present invention in the sample can be measured.

Another EIA method will be mentioned hereinafter. A sample is brought into contact with a carrier (such as an assay plate) to immobilize the proteins of the present invention in the sample on the carrier. Then, the first antibodies are added thereto to form complexes of the protein according to the present invention and the first antibody. To the complexes are added anti-first antibody antibodies (second antibodies) labeled with an enzyme (such as peroxidase), to react with the complexes to form "protein of the present invention/first antibody/second antibody" complexes. To the resulting "protein of the present invention/first antibody/second antibody" complexes is added a substrate for the enzyme label (such as peroxidase), and the absorbance or fluorescent strength of products of the enzymatic reaction is measured, whereby enzymatic activities of the enzyme labels attached to the "protein of the present invention/first antibody/second antibody" complexes are measured. A series of the above procedures is carried out in advance for a standard solution containing a known amount of the protein according to the present invention, and a standard curve based on the relationship between the protein of the present invention and the absorbance or fluorescent strength is prepared. A comparison is made between the standard curve and the absorbance or fluorescent strength for a sample containing an unknown amount of the proteins according to the present invention, and the amount of the proteins according to the present invention in the sample is measured.

Further, an RIA method will be mentioned hereinafter. A sample is added to the first antibodies immobilized on a carrier (such as a test tube), and the first antibodies are bound to the proteins of the present invention to form complexes. To the complexes are added the second antibodies labeled with radioactive isotope (such as $^{125}$I), to react with the complexes to form "first antibody/protein of the present invention/second antibody" complexes. A radioactivity (such as γ-radioactivity) of the resulting "first antibody/protein of the present invention/second antibody" complexes is measured. A series of the above procedures is carried out in advance for a standard solution containing a known amount of the protein according to the present invention, and a standard curve based on the relationship between the protein of the present invention and the radioactivity is prepared. A comparison is made between the standard curve and the radioactivity for a sample containing an unknown amount of the proteins according to the present invention, and the amount of the proteins according to the present invention in the sample is measured.

Another RIA method will be mentioned hereinafter. A sample is brought into contact with a carrier (such as a test tube) to immobilize the proteins of the present invention in the sample on the carrier. Then, the first antibodies are added thereto to form complexes of the protein according to the present invention and the first antibody. To the complexes are added anti-first antibody antibodies (second antibodies) labeled with a radioactive isotope (such as $^{125}$I), to react with the complexes to form "protein of the present invention/first antibody/second antibody" complexes. A radioactivity (such as γ-radioactivity) of the resulting "protein of the present invention/first antibody/second antibody" complexes is measured. A series of the above procedures is carried out in advance for a standard solution containing a known amount of the protein according to the present invention, and a standard curve based on the relationship between the protein in the present invention and the radioactivity is prepared. A comparison is made between the standard curve and the radioactivity for a sample containing an unknown amount of the proteins according to the present invention, and the amount of the proteins according to the present invention in the sample is measured.

EXAMPLES

The present invention now will be further illustrated by, but is by no means limited to, the following Examples.

Example 1

Isolation and Identification of Activated Human Macrophage-Specific Novel Genes (1) Preparation of mRNA Derived from Macrophages Stimulated by Lipopolysaccharide (LPS)

From 1 liter of blood derived from a healthy person as a starting material, peripheral blood monocytes were prepared using a commercially available reagent for preparing peripheral blood monocytes (Lymphoprep; Nycomed, Oslo, Norway). The obtained peripheral blood monocytes were suspended in an RPM1640 medium containing 10 μg/mL LPS (Difco Laboratories, Detroit, Mich., USA) and 10% fetal calf serum (FCS) so that the concentration of cells became $10^6$ cells/mL. To each plastic dish, 20 mL of the cell suspension was poured and cultured under the condition of 37° C. and 5% $CO_2$.

After culturing for 3 hours, the supernatant was discarded, and adherent cells (i.e., macrophages stimulated by LPS) were washed three times with 20 mL of a phosphate-buffered saline (PBS). After 3 mL of a solution for cell lysis [4 mol/L guanidine isothiocyanate, and 30 mmol/L sodium acetate (pH 4.8)] was added, suction and ejection were repeated three times using a syringe with a needle. The lysate was put on 1.2 mL of a 5.7 mol/L cesium chloride buffer (pH 4.8) in a ultracentrifuge 5PA tube (Hitachi Koki; Katsuta, Japan). After centrifuging for 18 hours (20° C., 38000 rpm), the supernatant in the centrifuge tube was discarded. The pellet in the centrifuge tube was dissolved in 200 μL of sterile water to collect RNA. From 1 L of blood, approximately 1 mg of total RNA (i.e., total RNA derived from macrophages stimulated by LPS) was obtained.

Then, using a commercially available kit for preparing mRNA [Poly(A) Quik mRNA Isolation Kit; Stratagene, La Jolla, Calif., USA], 15 μg of mRNA (i.e., mRNA derived from macrophages stimulated by LPS) was prepared from 500 μg of the total RNA.

(2) Preparation of a Phage cDNA Library

A phage cDNA library was prepared using 5 μg of the obtained mRNA (15 μg) derived from macrophages stimulated by LPS. Commercially available kits (ZAP Express cDNA Synthesis Kit and ZAP Express cDNA Gigapack III Gold Cloning Kit; Stratagene) were used to prepare the phage cDNA library.

(3) Analysis of Partial Base Sequences of cDNAs

To analyze base sequences of cDNAs derived macrophages stimulated by LPS, approximately 1000 phage plaques were picked up at random and cDNAs were recovered as a phagemid by a conventional method. With respect to the recovered approximately 1000 cDNAs derived macrophages stimulated by LPS, 400 to 500 bases from the 5' terminus and 3' terminus of the cDNAs were analyzed, respectively, using a commercially available kit for determining base sequences (Dye Terminator Cycle Sequencing kit; Perkin Elmer Japan, Urayasu). The DAN homology search of the obtained sequences was carried out using BLAST (basic local alignment tool) in NCBI (National Center for Biotechnology Information; http://inhouse.ncbi.nlm.nih.gov) and found 63 unknown novel genes.

(4) Analysis by Northern Blotting

Total RNA derived macrophages stimulated by LPS were prepared in accordance with the procedure for preparing total RNA derived macrophages stimulated by LPS described in Example (1). Further, total RNAs derived macrophages not stimulated by LPS were prepared in accordance with the procedure for preparing total RNA derived macrophages stimulated by LPS described in Example (1), except for using an RPM1640 medium containing 10% FCS instead of the RPM1640 medium containing 10 μg/mL LPS and 10% FCS. The total RNA derived macrophages stimulated by LPS (10 μg/mL LPS) and the total RNA derived macrophages not stimulated by LPS were electrophoresed on a formaldehyde/agarose gel and transferred onto a nylon membrane filter by a conventional method.

The filter onto which the RNAs were transferred was heat-treated at 80° C. under reduced pressure for 2 hours, and immersed in a commercially available solution for prehybridization (Hybrisol I; Oncor, Gaithersburg, Md., USA) to perform prehybridization at 42° C. for 3 hours. Then, the novel genes obtained in Example 1(3) labeled with isotope $^{32}$P using a random primed labeling kit (Boehringer Mannheim; Germany) were respectively added, and hybridization was carried out overnight at 42° C. On the next day, the filter was twice washed with 2×SSC (standard sodium citrate) containing 0.1% sodium dodecyl sulfate (SDS) at room temperature for 20 minutes, and further, twice washed with 0.2×SSC containing 0.1% SDS at 65° C. for 20 minutes. The washed filter was wrapped in a wrap, and autoradiography was performed overnight at −80° C.

As a result, it was found that, among 63 novel genes obtained in Example 1(3), three genes were those whose expression was induced by the LPS-stimulation. The results of northern blotting with respect to the three novel genes (NLG-1-1, NLG-1-2, and NLG-2) are shown in FIG. 1. In FIG. 1, the symbol "+" means "stimulated by LPS", the symbol "−" means "not stimulated by LPS", and "Origin" means "starting point of electrophoresis". The lengths of the mRNAs of the three novel genes (NLG-1-1, NLG-1-2, and NLG-2) were approximately 2.3 kb, approximately 2.3 kb, and approximately 0.7 kb, respectively.

Figure 2:
FIG. 2 shows the results of electrophoresis wherein the tissue-specific expression of three novel genes of the present invention was detected by a northern blotting method.

Further, the tissue-specific expression was examined. As shown in FIG. 2, the genes NLG-1-1 and NLG-1-2 were weakly expressed in all tissues examined [i.e., spleen (lane 1), thymus (lane 2), prostate (lane 3), testis (lane 4), ovary (lane 5), small intestine (lane 6), large intestine (lane 7) and peripheral blood lymphocyte (lane 8)]. On the contrary, the gene NLG-2 was strongly expressed in testis (lane 4) and large intestine (lane 7), but not expressed in the other tissues.

(5) Determination of Full-length Base Sequences

The full-length base sequences of the three novel genes (LG-1-1, NLG-1-2, and NLG-2) were determined by a conventional method.

The genes NLG-1-1 and NLG-1-2 consist of 2180 bp and 1970 bp, respectively. The concrete base sequences thereof are those of SEQ ID NO: 1 and SEQ ID NO: 3 in the sequence listing, respectively. As the result of a homology search of the genes NLG-1-1 and NLG-1-2, the 193rd to 2139th base sequence of the gene NLG-1-1 was found to be completely identical to the 9th to 1955th base sequence of the gene NLG-1-2. It is presumed that two mRNAs are transcribed from a chromosomal gene in accordance with an alternative splicing. The gene NLG-1-1 encodes a protein consisting of 481 amino acid residues having the amino acid sequence of SEQ ID NO: 2 in the sequence listing. The gene NLG-1-2 encodes a protein consisting of 390 amino acid residues having the amino acid sequence of SEQ ID NO: 4 in the sequence listing.

Further, the gene NLG-2 consists of 652 bp, and the concrete base sequence thereof is that of SEQ ID NO: 5 in the sequence listing. The gene NLG-2 encodes a protein consisting of 83 amino acid residues having the amino acid sequence of SEQ ID NO: 6 in the sequence listing.

Example 2

Expression of the Genes NLG-1-1 and NLG-2 in an Animal Cell

In this example, the genes NLG-1-1 and NLG-2 were expressed using COS-1 (Dainippon pharmaceutical, Suita, Osaka, Japan) as an animal cell and a pQBI25-fN3rsGFP vector (Quantum biotechnologies, Montreal, Quebec, Canada) by the following procedure. This was because when the above vector is used, a desired gene can be expressed in the form of a fused protein with a green fluorescent protein (GFP), and therefore, locations of the desired gene products can be observed by tracing the green fluorescence.

Each cDNA of genes NLG-1-1 and NLG-2 was prepared by a reverse transcription PCR (RT-PCR) method in accordance with the following procedure. An mRNA was prepared from human peripheral blood monocytes (PBMC) stimulated by LPS for 3 hours. A cDNA synthesized from the mRNA using a commercially available cDNA synthesis kit (SMART PCR cDNA synthesis kit; Clontech, Palo alto, Calif., USA) was used as a template.

As primers, an NLG-2 forward primer consisting of the sequence:
5'-CACGGATCCATTCTTCGCTGAAGTCATCATGAGC-3' (SEQ ID NO: 7), an NLG-2 reverse primer consisting of the sequence:
5'-GTGGAATTCTTTGGTCACCCTTTGGACATTTTGC-3' (SEQ ID NO: 8), an NLG-1-1 forward primer consisting of the sequence:
5'-CACGGATCCTTCTTTACAACGAAATGATGCTCAAG-3' (SEQ ID NO: 9), and an NLG-1-1 reverse primer consisting of the sequence:
5'-GTGGAATTCGGAGAGATTTGTGATAGAATTATTACATGC-3' (SEQ ID NO: 10) were used.

Using a commercially available reagent for PCR (Advantage cDNA polymerase Mix; Clontech), PCR was carried out by repeating a cycle consisting of a denaturation step (94° C., 30 seconds) and an annealing and elongation step (68° C., 2 minutes), 30 times.

The obtained PCR product was digested with restriction enzymes BamHI (Takarashuzo, Chuo-ku, Tokyo, Japan) and EcoRI (Takarashuzo), and cloned in a pQBI25-fN3rsGFP vector using a commercially available kit (DNA ligation kit Ver. 2; Takarashuzo) to use for the following experiments.

On the day before a gene transfer, COS-1 cells were plated on a 6-well plate so that the concentration of cells became 1×10$^6$ cells/well. In each well of the 6-well plate, an autoclaved cover glass was placed, and cells were cultured on the cover glass. On the next day, the previously obtained vector was transferred to cos-1 cells using a commercially available reagent for transfection (LipofectAMINE reagent; Gibco BRL, Rockville, Md., USA). After 3 days from the transfer, cells on the cover glass were fixed in PBS containing 4% (v/v) formalin for 30 minutes, treated in PBS containing 0.2% (v/v) Triton X-100 for 30 minutes, and treated in a blocking reagent (Block Ace; Dainippon pharmaceutical) containing 20% (v/v) normal goat serum (Vector Laboratories, Burlingame, Calif., USA) for 30 minutes.

For immunostaining a mitochondrion, an anti-cytochrome c antibody (Santa Cruz Biotechnology, Santa Cruz, Calif., USA) and a Texas red-labeled anti-rabbit IgG antibody (Vector Laboratories) were used. For immunostaining an endoplasmic reticulum, an anti-calreticulin antibody (Upstate Biotechnology, Lake Placid, N.Y., USA) and a Texas red-labeled anti-rabbit IgG antibody (Vector Laboratories) were used. For immunostaining a Golgi apparatus, an anti-Golgi 58K protein antibody (Sigma, St. Louis, Mo., USA) and a Texas red-labeled anti-mouse IgG antibody (Kirkegaard & Perry Laboratories, Gaithersburg, Md., USA) were used.

For staining a nucleus, propidium iodide (Wako Pure Chemical Industries, Osaka, Osaka, Japan) was used. For staining cytoplasm, hydroethidine (Polysciences, Warrington, Pa., USA) was used.

Figure 3:
FIGS. 3A–D provide micrographs showing the results of the expression of the gene NLG-1-1 of the present invention in COS-1 cells.
Figure 4:
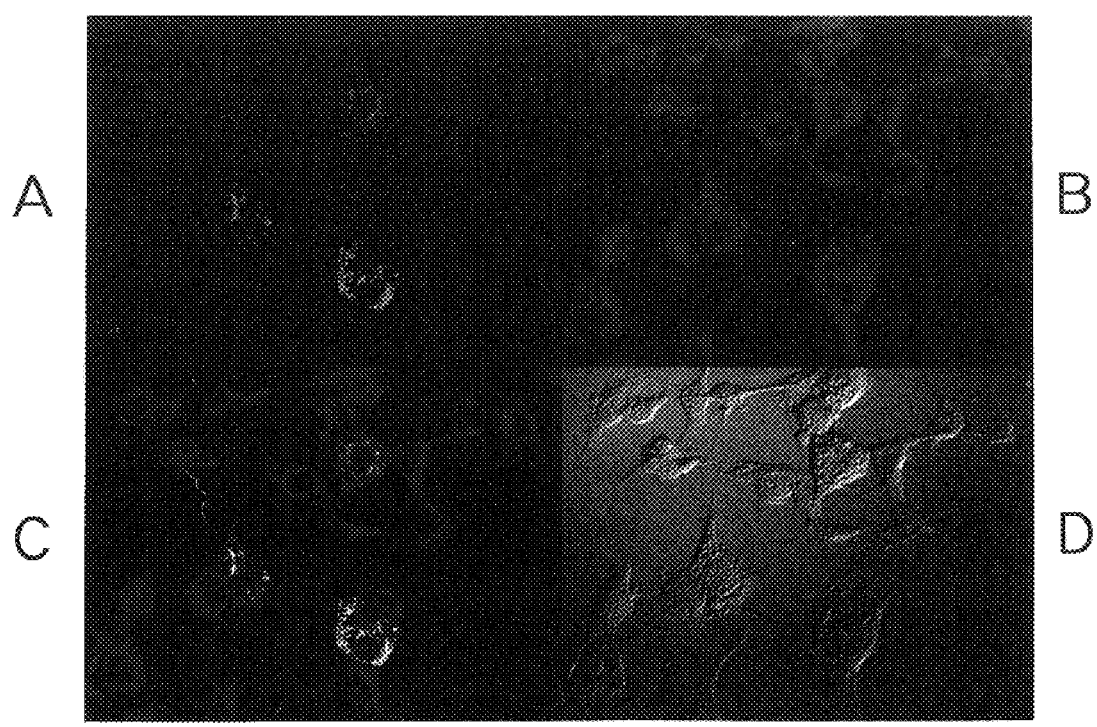
FIGS. 4A–D provide micrographs showing the results of the expression of the gene NLG-2 of the present invention in COS-1 cells.

The cover glass was mounted on a slide glass, and observed with a confocal laser scanning microscope FV500 (Olympus Optical Company Limited, Chiyoda-ku, Tokyo, Japan). The state of COS-1 cells in which the gene NLG-1-1 was expressed is shown in FIG. 3. The state of COS-1 cells in which the gene NLG-2 was expressed is shown in FIG. 4. In FIGS. 3 and 4, "A" is a green fluorograph showing the expression of the fusion protein of GFP with the protein encoded by the gene NLG-1-1 or NLG-2; "B" is a red fluorograph wherein mitochondria were stained; "C" is a combination of the above fluorographs A and B; and "D" is a figure of differential calculus interference.

As shown in FIG. 3A, the expression of the gene NLG-1-1 was observed around the nucleus. Further, the green fluorograph in FIG. 3A and the red fluorograph (the fluorograph wherein mitochondria were stained) in FIG. 3B accorded well. In FIG. 3C, the areas wherein fluorographs A and B accorded were shown in yellow. On the contrary, the fluorograph wherein endoplasmic reticula were stained, the fluorograph wherein Golgi apparatus were stained, the image wherein nuclei were stained, or the image wherein cytoplasm was stained did not accord with the green fluorograph in FIG. 3A. Accordingly, it was found that the protein encoded by the gene NLG-1–1 was localized in mitochondria.

Further, as apparent from FIG. 4, it was found that the protein encoded by the gene NLG-2 was localized in mitochondria, as the protein encoded by the gene NLG-1-1.

Example 3

Determination of the Chromosomal Locus of the Gene NLG-1-1

Figure 5:
FIGS. 5A and B provide micrographs showing the results of a FISH analysis of the gene NLG-1-1 of the present invention.
Figure 5:
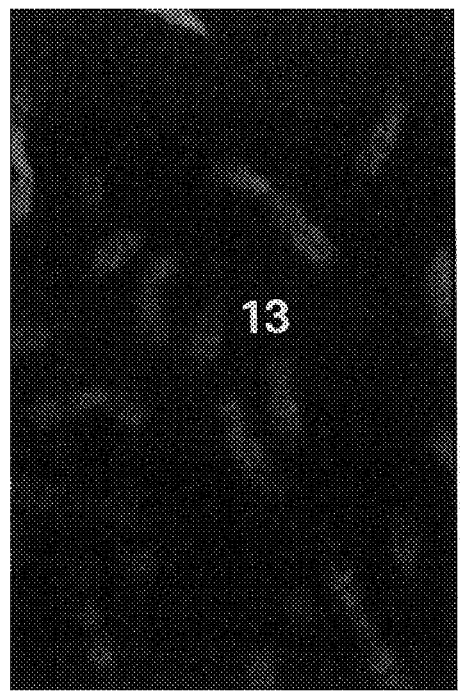

The chromosomal locus of the gene NLG-1-1 was determined by a FISH (fluorescence in situ hybridization) analysis [Chromosoma., 102, 325–332 (1993)]. The gene was located on 13q22. The results were shown in FIG. 5. In FIG. 5, "A" is the result of DAPI (4',6-diamidino-2-phenylindole) staining, and "B" is the result of the FISH signal. The arrow in FIG. 5A denotes the chromosomal locus of the gene NLG-1-1, and the number "13" denotes that it is the thirteenth chromosome.

Example 4

Determination of Expression of the Genes NLG-1-1, NLG-1-2, and NLG-2 in Patients Suffering from Septicemia From 20 mL of each blood collected from four healthy persons and four patients suffering from septicemia as a starting material, peripheral blood monocytes were prepared, and then approximately 20 µg of total RNA was respectively prepared from the peripheral blood monocytes in accordance with the procedure described in Example 1(1).

Using 10 µg of each RNA, northern blotting was carried out in accordance with the procedure described in Example 1(4).

Figure 6:
FIGS. 6A–C provide photographs showing the results of electrophoresis wherein the expression of three novel genes of the present invention in healthy persons and patients suffering from septicemia was detected by a northern blotting method.
Figure 6:
Figure 6:

The results are shown in FIG. 6. In FIG. 6, (A) shows the result using the gene NLG-1-1 as a probe. Similarly, (B) and (C) show the results using the genes NLG-1-2 and NLG-2 as a probe, respectively. Further, in FIG. 6, lanes 1 to 4 denote the results of RNAs derived from the healthy persons, and lanes 5 to 8 denote the results of RNAs derived from the patients suffering from septicemia.

As shown in FIG. 6, three novel genes (NLG-1-1, NLG-1-2, and NLG-2) of the present invention were not expressed in all four healthy persons, but were strongly expressed in all four patients suffering from septicemia. These results show that these genes of the present invention may be used for the diagnosis of a bacterial infection or a judgment of prognosis by analyzing the expression of the genes.

INDUSTRIAL APPLICABILITY

It is known that life phenomena caused by an LPS-stimulation are similar to those in inflammation. In fact, the genes having an expression that is induced by an LPS-stimulation specifically at a macrophage playing a central role in inflammation include almost all genes encoding proteins leading to inflammatory diseases, for example, an inflammatory cytokine (TNF, IL-1, IL-6, IL-18), a chemokine (IL-8, MCP), a secretory protein, such as a collagenase abnormally produced at a diseased part of rheumatoid arthritis which is an inflammatory disease, an NO synthase which is an intracellular protein and produces NO (nitrogen monoxide) causing an inflammation, cylooxygenese (COXII) producing a prostaglandin, an NF-kB, i.e., a gene-transcription factor participating in an expression of a gene encoding an inflammatory protein, or the like.

Clinical development for inhibitors of the above proteins as an antiinflammatory drug has been intensively carried out, and many inhibitors are undergoing a clinical study. For example, an anti-TNF antibody or an inhibitor of NO synthase is already being used as a medicament for treating an inflammatory disease. Further, a clinical development of a collagenase inhibitor as an inhibitor for a cancer metastasis, and of a COXII inhibitor as an anticancer drug is already being carried out. These suggest that there is a strong possibility that the novel genes having an expression that is induced by an LPS-stimulation and proteins according to the present invention also participate in the outbreak and/or deterioration of an inflammatory disease, an allergy disease, or a cancer.

The possibility exists that the first and second novel proteins of the present invention take part in an intracellular signal transduction system of an LPS. Further, the possibility exists that the third novel protein of the present invention takes part in an intracellular electron transportation and/or a radical production. Therefore, the proteins as above are different from a target of a conventional development of an antiinflammatory drug, whereas inhibitors of the proteins as above will be a new type of antiinflammatory drug. Further, an examination of an expression of the genes encoding the proteins as above in a human clinical sample by means of a reverse transcription PCR (RT-PCR), a northern blotting, a dot blotting, or a DNA microarray would make it possible to carry out a diagnosis of an inflammation, an allergy, or a cancer. Furthermore, an antibody against the protein as above could be used to carry out a diagnosis of an inflammation, an allergy, or a cancer. Still further, antisense DNAs of the genes encoding the proteins as above could be used in a treatment of an inflammation, an allergy, or a cancer (including a gene therapy).

The probe or the antibody according to the present invention may be used to carry out a diagnosis of a bacterial infection, such as septicemia, pneumonia, urinary tract infection, myelitis, or tympanitis, or a judgment of prognosis. The proteins of the present invention are useful for preparing the antibodies of the present invention, and the novel genes, plasmids, and transformants of the present invention are useful for preparing the proteins of the present invention.

As above, the present invention is explained with reference to particular embodiments, but modifications and improvements obvious to those skilled in the art are included in the scope of the present invention.

What is claimed is:

1. An isolated nucleic acid which encodes the protein of SEQ ID NO:2.

2. The nucleic acid according to claim 1, consisting of nucleotides 37–1479 of SEQ ID NO:1.

3. A plasmid comprising said nucleic acid according to claim 1.

4. A transformed host cell comprising said plasmid according to claim 3.

5. A plasmid comprising said nucleic acid according to claim 2.

* * * * *

UNITED STATES PATENT AND TRADEMARK OFFICE
CERTIFICATE OF CORRECTION

PATENT NO.        : 7,135,559 B2  
APPLICATION NO.   : 10/220862  
DATED             : November 14, 2006  
INVENTOR(S)       : Kunitaka Hirose et al.

Page 1 of 1

It is certified that error appears in the above-identified patent and that said Letters Patent is hereby corrected as shown below:

Title page, item [73] Assignee:

Delete "Kureha Chemical Industry Co., Ltd., Tokyo (JP)" and substitute

-- Kureha Corporation, Tokyo (JP) --.

Signed and Sealed this

Ninth Day of January, 2007

JON W. DUDAS  
*Director of the United States Patent and Trademark Office*

SEQUENCE LISTING

<160> NUMBER OF SEQ ID NOS: 10

<210> SEQ ID NO 1
<211> LENGTH: 2180
<212> TYPE: DNA
<213> ORGANISM: Homo sapiens
<220> FEATURE:
<221> NAME/KEY: CDS
<222> LOCATION: (37)..(1482)

<400> SEQUENCE: 1

```
ggcacgagct gaactgaacc tcttctttac aacgaa atg atg ctc aag tct atc           54
                                       Met Met Leu Lys Ser Ile
                                        1               5 aca gaa agc ttt gcc aca gca atc cat ggc ttg aaa gtg gga cac ctg          102
Thr Glu Ser Phe Ala Thr Ala Ile His Gly Leu Lys Val Gly His Leu
             10                  15                  20 aca gat cgt gtt att cag agg agc aag agg atg att cta gac act ctg         150
Thr Asp Arg Val Ile Gln Arg Ser Lys Arg Met Ile Leu Asp Thr Leu
         25                  30                  35 ggt gct ggg ttc ctg gga acc act acg gaa gtg ttt cac ata gcc agc         198
Gly Ala Gly Phe Leu Gly Thr Thr Thr Glu Val Phe His Ile Ala Ser
     40                  45                  50 caa tat agc aag atc tac agt tcc aac ata tcc agc act gta tgg ggt         246
Gln Tyr Ser Lys Ile Tyr Ser Ser Asn Ile Ser Ser Thr Val Trp Gly
 55                  60                  65                  70 cag cca gac atc agg ctc ccg ccc aca tat gct gct ttt gtg aac ggt         294
Gln Pro Asp Ile Arg Leu Pro Pro Thr Tyr Ala Ala Phe Val Asn Gly
                 75                  80                  85 gtg gct att cac tcc atg gat ttt gat gac acg tgg cac cct gcc acc         342
Val Ala Ile His Ser Met Asp Phe Asp Asp Thr Trp His Pro Ala Thr
             90                  95                 100 cac cct tct ggg gct gtc ctt cct gtc ctc aca gct tta gca gaa gcc         390
His Pro Ser Gly Ala Val Leu Pro Val Leu Thr Ala Leu Ala Glu Ala
        105                 110                 115 ctg cca agg agt cca aag ttt tct ggc ctt gac ctg ctg ctg gct ttc         438
Leu Pro Arg Ser Pro Lys Phe Ser Gly Leu Asp Leu Leu Leu Ala Phe
    120                 125                 130 aat gtt ggt att gaa gtg caa ggc cga tta ctg cat ttc gcc aag gag         486
Asn Val Gly Ile Glu Val Gln Gly Arg Leu Leu His Phe Ala Lys Glu
135                 140                 145                 150 gcc aat gac atg cca aag aga ttc cat ccc cct tcc gtg gta gga acg         534
Ala Asn Asp Met Pro Lys Arg Phe His Pro Pro Ser Val Val Gly Thr
                155                 160                 165 ttg ggt agt gct gct gct gca tcc aag ttt tta gga ctt agc tcg aca         582
Leu Gly Ser Ala Ala Ala Ala Ser Lys Phe Leu Gly Leu Ser Ser Thr
            170                 175                 180 aag tgc cga gaa gct ctg gcc att gct gtt tcc cat gct ggg gca ccc         630
Lys Cys Arg Glu Ala Leu Ala Ile Ala Val Ser His Ala Gly Ala Pro
        185                 190                 195 atg gcc aat gct gcc acc cag acc aag ccc ctc cac att ggc aat gct         678
Met Ala Asn Ala Ala Thr Gln Thr Lys Pro Leu His Ile Gly Asn Ala
    200                 205                 210 gcc aag cat ggg ata gaa gct gca ttt ttg gca atg ttg ggt ctc caa         726
Ala Lys His Gly Ile Glu Ala Ala Phe Leu Ala Met Leu Gly Leu Gln
215                 220                 225                 230 gga aac aag cag gtc ttg gac ttg gag gca gga ttt ggg gcc ttt tat         774
Gly Asn Lys Gln Val Leu Asp Leu Glu Ala Gly Phe Gly Ala Phe Tyr
                235                 240                 245
```

-continued gcc aac tat tcc cca aaa gtc ctt cca agc ata gct tcc tac agt tgg       822
Ala Asn Tyr Ser Pro Lys Val Leu Pro Ser Ile Ala Ser Tyr Ser Trp
            250                 255                 260 ctg ctg gac cag cag gac gtg gcc ttt aag cgt ttt cct gca cat tta       870
Leu Leu Asp Gln Gln Asp Val Ala Phe Lys Arg Phe Pro Ala His Leu
265                 270                 275 tct acc cac tgg gtg gca gac gca gct gca tct gtg aga aag cac ctt       918
Ser Thr His Trp Val Ala Asp Ala Ala Ala Ser Val Arg Lys His Leu
        280                 285                 290 gta gca gag aga gcc ctg ctt cca act gac tac att aag aga att gtg       966
Val Ala Glu Arg Ala Leu Leu Pro Thr Asp Tyr Ile Lys Arg Ile Val
295                 300                 305                 310 ctc agg ata cca aat gtc cag tat gta aac agg ccc ttt cca gtt tcg      1014
Leu Arg Ile Pro Asn Val Gln Tyr Val Asn Arg Pro Phe Pro Val Ser
                315                 320                 325 gag cat gaa gcc cgt cat tca ttc cag tat gtg gcc tgt gcc atg ctg      1062
Glu His Glu Ala Arg His Ser Phe Gln Tyr Val Ala Cys Ala Met Leu
            330                 335                 340 ctt gat ggt ggc atc act gtc ccc tca ttc cat gaa tgc cag atc aac      1110
Leu Asp Gly Gly Ile Thr Val Pro Ser Phe His Glu Cys Gln Ile Asn
                345                 350                 355 agg cca cag gtg aga gag ctg ctc agt aag gtg gag ctg gag tac cct      1158
Arg Pro Gln Val Arg Glu Leu Leu Ser Lys Val Glu Leu Glu Tyr Pro
        360                 365                 370 ccg gac aac ttg cca agc ttc aac ata ctg tac tgt gaa ata agt gtc      1206
Pro Asp Asn Leu Pro Ser Phe Asn Ile Leu Tyr Cys Glu Ile Ser Val
375                 380                 385                 390 acc ctc aag gat gga gcc acc ttc aca gat cgc tct gat acc ttc tat      1254
Thr Leu Lys Asp Gly Ala Thr Phe Thr Asp Arg Ser Asp Thr Phe Tyr
                395                 400                 405 ggg cac tgg aga aaa cca ctg agc cag gag gac cta gag gaa aag ttc      1302
Gly His Trp Arg Lys Pro Leu Ser Gln Glu Asp Leu Glu Glu Lys Phe
            410                 415                 420 aga gcc aat gcc tcc aag atg ctg tcc tgg gac aca gtg gaa agc ctt      1350
Arg Ala Asn Ala Ser Lys Met Leu Ser Trp Asp Thr Val Glu Ser Leu
                425                 430                 435 ata aag ata gtc aaa aat cta gaa gac cta gaa gac tgt tct gtg tta      1398
Ile Lys Ile Val Lys Asn Leu Glu Asp Leu Glu Asp Cys Ser Val Leu
        440                 445                 450 act aca ctt ctc aaa gga ccc tct cca cca gag gta gct tca aac tct      1446
Thr Thr Leu Leu Lys Gly Pro Ser Pro Pro Glu Val Ala Ser Asn Ser
455                 460                 465                 470 cca gca tgt aat aat tct atc aca aat ctc tcc tgaggcttac caacatctaa    1499
Pro Ala Cys Asn Asn Ser Ile Thr Asn Leu Ser
                475                 480 atgactttgc atttggggag attcaatgat ttggtttgta aagcaagggt ctgctgcttg    1559
gttttcccag gaaaaatgaa caaagatgga gagagtccag aaacagaact acatatatct   1619
ggaaggagcc ttctcctgaa aattttgcag gacagttcca cttacctaaa tcaagatgaa   1679
acacacacac aaaaatgagt ttgtaagcat tcacaagggt gaaattcaac tcacctgtga   1739
tttacttata aaattaatct cttcatagga attatgtgtg gacttcatga gcctcaaggt   1799
tttagaggga tgtgaacctg catgtatatt ttctgacagt ggagagggct ctggtgcatt   1859
gtgtcaccaa cagatctcct agaccatggc ttattaccaa gccctccaca gtgcaagggg   1919
tgctactggg gaatgggtgg gtttaaatcc tgcctctgcc attcactaga tgtagccttg   1979
agcatgttac cattagccct ctgcctcagt ttccctattt gtcaagccga agtaaaaagc   2039
agtctggaaa aatcgcattt tggctctaga acccatggtc ttaagcactg caatatatca   2099
cctttcagta taaaatatt tgaatcagag ttgcaataaa gaatgaaaag gaaaaaagag    2159
aagtaaaaaa aaaaaaaaaa a    2180

<210> SEQ ID NO 2
<211> LENGTH: 481
<212> TYPE: PRT
<213> ORGANISM: Homo sapiens

<400> SEQUENCE: 2

```
Met Met Leu Lys Ser Ile Thr Glu Ser Phe Ala Thr Ala Ile His Gly
 1               5                  10                  15

Leu Lys Val Gly His Leu Thr Asp Arg Val Ile Gln Arg Ser Lys Arg
             20                  25                  30

Met Ile Leu Asp Thr Leu Gly Ala Gly Phe Leu Gly Thr Thr Thr Glu
         35                  40                  45

Val Phe His Ile Ala Ser Gln Tyr Ser Lys Ile Tyr Ser Ser Asn Ile
     50                  55                  60

Ser Ser Thr Val Trp Gly Gln Pro Asp Ile Arg Leu Pro Pro Thr Tyr
 65                  70                  75                  80

Ala Ala Phe Val Asn Gly Val Ala Ile His Ser Met Asp Phe Asp Asp
                 85                  90                  95

Thr Trp His Pro Ala Thr His Pro Ser Gly Ala Val Leu Pro Val Leu
            100                 105                 110

Thr Ala Leu Ala Glu Ala Leu Pro Arg Ser Pro Lys Phe Ser Gly Leu
        115                 120                 125

Asp Leu Leu Ala Phe Asn Val Gly Ile Glu Val Gln Gly Arg Leu
    130                 135                 140

Leu His Phe Ala Lys Glu Ala Asn Asp Met Pro Lys Arg Phe His Pro
145                 150                 155                 160

Pro Ser Val Val Gly Thr Leu Gly Ser Ala Ala Ala Ser Lys Phe
                165                 170                 175

Leu Gly Leu Ser Ser Thr Lys Cys Arg Glu Ala Leu Ala Ile Ala Val
            180                 185                 190

Ser His Ala Gly Ala Pro Met Ala Asn Ala Ala Thr Gln Thr Lys Pro
        195                 200                 205

Leu His Ile Gly Asn Ala Ala Lys His Gly Ile Glu Ala Ala Phe Leu
    210                 215                 220

Ala Met Leu Gly Leu Gln Gly Asn Lys Gln Val Leu Asp Leu Glu Ala
225                 230                 235                 240

Gly Phe Gly Ala Phe Tyr Ala Asn Tyr Ser Pro Lys Val Leu Pro Ser
                245                 250                 255

Ile Ala Ser Tyr Ser Trp Leu Leu Asp Gln Gln Asp Val Ala Phe Lys
            260                 265                 270

Arg Phe Pro Ala His Leu Ser Thr His Trp Val Ala Asp Ala Ala
        275                 280                 285

Ser Val Arg Lys His Leu Val Ala Glu Arg Ala Leu Leu Pro Thr Asp
    290                 295                 300

Tyr Ile Lys Arg Ile Val Leu Arg Ile Pro Asn Val Gln Tyr Val Asn
305                 310                 315                 320

Arg Pro Phe Pro Val Ser Glu His Glu Ala Arg His Ser Phe Gln Tyr
                325                 330                 335

Val Ala Cys Ala Met Leu Leu Asp Gly Gly Ile Thr Val Pro Ser Phe
            340                 345                 350
```

```
His Glu Cys Gln Ile Asn Arg Pro Gln Val Arg Glu Leu Leu Ser Lys
            355                 360                 365

Val Glu Leu Glu Tyr Pro Pro Asp Asn Leu Pro Ser Phe Asn Ile Leu
        370                 375                 380

Tyr Cys Glu Ile Ser Val Thr Leu Lys Asp Gly Ala Thr Phe Thr Asp
385                 390                 395                 400

Arg Ser Asp Thr Phe Tyr Gly His Trp Arg Lys Pro Leu Ser Gln Glu
                405                 410                 415

Asp Leu Glu Glu Lys Phe Arg Ala Asn Ala Ser Lys Met Leu Ser Trp
            420                 425                 430

Asp Thr Val Glu Ser Leu Ile Lys Ile Val Lys Asn Leu Glu Asp Leu
        435                 440                 445

Glu Asp Cys Ser Val Leu Thr Thr Leu Leu Lys Gly Pro Ser Pro Pro
    450                 455                 460

Glu Val Ala Ser Asn Ser Pro Ala Cys Asn Asn Ser Ile Thr Asn Leu
465                 470                 475                 480

Ser
```

<210> SEQ ID NO 3
<211> LENGTH: 1970
<212> TYPE: DNA
<213> ORGANISM: Homo sapiens
<220> FEATURE:
<221> NAME/KEY: CDS
<222> LOCATION: (126)..(1298)

<400> SEQUENCE: 3

```
ggcacgaggc cagccaatat agcaagatct acagttccaa catatccagc actgtttggg        60
gtcagccaga catcaggctc ccgcccacat atgctgcttt tgtgaacggt gtggctattc       120 actcc atg gat ttt gat gac acg tgg cac cct gcc acc cac cct tct ggg      170
      Met Asp Phe Asp Asp Thr Trp His Pro Ala Thr His Pro Ser Gly
      1               5                   10                  15 gct gtc ctt cct gtc ctc aca gct tta gca gaa gcc ctg cca agg agt        218
Ala Val Leu Pro Val Leu Thr Ala Leu Ala Glu Ala Leu Pro Arg Ser
            20                  25                  30 cca aag ttt tct ggc ctt gac ctg ctg ctg gct ttc aat gtt ggt att        266
Pro Lys Phe Ser Gly Leu Asp Leu Leu Leu Ala Phe Asn Val Gly Ile
        35                  40                  45 gaa gtg caa ggc cga tta ctg cat ttc gcc aag gag gcc aat gac atg        314
Glu Val Gln Gly Arg Leu Leu His Phe Ala Lys Glu Ala Asn Asp Met
    50                  55                  60 cca aag aga ttc cat ccc cct tcc gtg gta gga acg ttg ggt agt gct        362
Pro Lys Arg Phe His Pro Pro Ser Val Val Gly Thr Leu Gly Ser Ala
65                  70                  75 gct gct gca tcc aag ttt tta gga ctt agc tcg aca aag tgc cga gaa        410
Ala Ala Ala Ser Lys Phe Leu Gly Leu Ser Ser Thr Lys Cys Arg Glu
                85                  90                  95 gct ctg gcc att gct gtt tcc cat gct ggg gca ccc atg gcc aat gct        458
Ala Leu Ala Ile Ala Val Ser His Ala Gly Ala Pro Met Ala Asn Ala
            100                 105                 110 gcc acc cag acc aag ccc ctc cac att ggc aat gct gcc aag cat ggg        506
Ala Thr Gln Thr Lys Pro Leu His Ile Gly Asn Ala Ala Lys His Gly
        115                 120                 125 ata gaa gct gca ttt ttg gca atg ttg ggt ctc caa gga aac aag cag        554
Ile Glu Ala Ala Phe Leu Ala Met Leu Gly Leu Gln Gly Asn Lys Gln
    130                 135                 140 gtc ttg gac ttg gag gca gga ttt ggg gcc ttt tat gcc aac tat tcc        602
Val Leu Asp Leu Glu Ala Gly Phe Gly Ala Phe Tyr Ala Asn Tyr Ser
```

```
                145                 150                 155
cca aaa gtc ctt cca agc ata gct tcc tac agt tgg ctg ctg gac cag       650
Pro Lys Val Leu Pro Ser Ile Ala Ser Tyr Ser Trp Leu Leu Asp Gln
160                 165                 170                 175 cag gac gtg gcc ttt aag cgt ttt cct gca cat tta tct acc cac tgg       698
Gln Asp Val Ala Phe Lys Arg Phe Pro Ala His Leu Ser Thr His Trp
                180                 185                 190 gtg gca gac gca gct gca tct gtg aga aag cac ctt gta gca gag aga       746
Val Ala Asp Ala Ala Ala Ser Val Arg Lys His Leu Val Ala Glu Arg
                195                 200                 205 gcc ctg ctt cca act gac tac att aag aga att gtg ctc agg ata cca       794
Ala Leu Leu Pro Thr Asp Tyr Ile Lys Arg Ile Val Leu Arg Ile Pro
            210                 215                 220 aat gtc cag tat gta aac agg ccc ttt cca gtt tcg gag cat gaa gcc       842
Asn Val Gln Tyr Val Asn Arg Pro Phe Pro Val Ser Glu His Glu Ala
        225                 230                 235 cgt cat tca ttc cag tat gtg gcc tgt gcc atg ctg ctt gat ggt ggc       890
Arg His Ser Phe Gln Tyr Val Ala Cys Ala Met Leu Leu Asp Gly Gly
240                 245                 250                 255 atc act gtc ccc tca ttc cat gaa tgc cag atc aac agg cca cag gtg       938
Ile Thr Val Pro Ser Phe His Glu Cys Gln Ile Asn Arg Pro Gln Val
                260                 265                 270 aga gag ctg ctc agt aag gtg gag ctg gag tac cct ccg gac aac ttg       986
Arg Glu Leu Leu Ser Lys Val Glu Leu Glu Tyr Pro Pro Asp Asn Leu
                275                 280                 285 cca agc ttc aac ata ctg tac tgt gaa ata agt gtc acc ctc aag gat      1034
Pro Ser Phe Asn Ile Leu Tyr Cys Glu Ile Ser Val Thr Leu Lys Asp
            290                 295                 300 gga gcc acc ttc aca gat cgc tct gat acc ttc tat ggg cac tgg aga      1082
Gly Ala Thr Phe Thr Asp Arg Ser Asp Thr Phe Tyr Gly His Trp Arg
        305                 310                 315 aaa cca ctg agc cag gag gac cta gag gaa aag ttc aga gcc aat gcc      1130
Lys Pro Leu Ser Gln Glu Asp Leu Glu Glu Lys Phe Arg Ala Asn Ala
320                 325                 330                 335 tcc aag atg ctg tcc tgg gac aca gtg aaa agc ctt ata aag ata gtc      1178
Ser Lys Met Leu Ser Trp Asp Thr Val Glu Ser Leu Ile Lys Ile Val
                340                 345                 350 aaa aat cta gaa gac cta gaa gac tgt tct gtg tta act aca ctt ctc      1226
Lys Asn Leu Glu Asp Leu Glu Asp Cys Ser Val Leu Thr Thr Leu Leu
                355                 360                 365 aaa gga ccc tct cca cca gag gta gct tca aac tct cca gca tgt aat      1274
Lys Gly Pro Ser Pro Pro Glu Val Ala Ser Asn Ser Pro Ala Cys Asn
            370                 375                 380 aat tct atc aca aat ctc tcc tgaggcttac caacatctaa atgactttgc         1325
Asn Ser Ile Thr Asn Leu Ser
        385                 390 atttggggag attcaatgat ttggtttgta aagcaagggt ctgctgcttg gttttcccag    1385
gaaaaatgaa caaagatgga gagagtccag aaacagaact acatatatct ggaaggagcc    1445
ttctcctgaa aattttgcag gacagttcca cttacctaaa tcaagatgaa acacacacac    1505
aaaaatgagt ttgtaagcat tcacaagggt gaaattcaac tcacctgtga tttacttata    1565
aaattaatct cttcatagga attatgtgtg gacttcatga gcctcaaggt tttagaggga    1625
tgtgaacctg catgtatatt ttctgacagt ggagagggct ctggtgcatt gtgtcaccaa    1685
cagatctcct agaccatggc ttattaccaa gccctccaca gtgcaagggg tgctactggg    1745
gaatgggtgg gtttaaatcc tgcctctgcc attcactaga tgtagccttg agcatgttac    1805
cattagccct ctgcctcagt ttccctattt gtcaagccga agtaaaaagc agtctggaaa    1865
```

-continued

```
aatcgcattt tggctctaga acccatggtc ttaagcactg caatatatca cctttcagta    1925
taaaaatatt tgaatcagag ttgcaataaa aaaaaaaaaa aaaaa                    1970
```

<210> SEQ ID NO 4
<211> LENGTH: 390
<212> TYPE: PRT
<213> ORGANISM: Homo sapiens

<400> SEQUENCE: 4

```
Met Asp Phe Asp Asp Thr Trp His Pro Ala Thr His Pro Ser Gly Ala
  1               5                  10                  15

Val Leu Pro Val Leu Thr Ala Leu Ala Glu Ala Leu Pro Arg Ser Pro
             20                  25                  30

Lys Phe Ser Gly Leu Asp Leu Leu Ala Phe Asn Val Gly Ile Glu
         35                  40                  45

Val Gln Gly Arg Leu Leu His Phe Ala Lys Glu Ala Asn Asp Met Pro
     50                  55                  60

Lys Arg Phe His Pro Pro Ser Val Val Gly Thr Leu Gly Ser Ala Ala
 65                  70                  75                  80

Ala Ala Ser Lys Phe Leu Gly Leu Ser Ser Thr Lys Cys Arg Glu Ala
                 85                  90                  95

Leu Ala Ile Ala Val Ser His Ala Gly Ala Pro Met Ala Asn Ala Ala
            100                 105                 110

Thr Gln Thr Lys Pro Leu His Ile Gly Asn Ala Ala Lys His Gly Ile
        115                 120                 125

Glu Ala Ala Phe Leu Ala Met Leu Gly Leu Gln Gly Asn Lys Gln Val
    130                 135                 140

Leu Asp Leu Glu Ala Gly Phe Gly Ala Phe Tyr Ala Asn Tyr Ser Pro
145                 150                 155                 160

Lys Val Leu Pro Ser Ile Ala Ser Tyr Ser Trp Leu Leu Asp Gln Gln
                165                 170                 175

Asp Val Ala Phe Lys Arg Phe Pro Ala His Leu Ser Thr His Trp Val
            180                 185                 190

Ala Asp Ala Ala Ser Val Arg Lys His Leu Val Ala Glu Arg Ala
        195                 200                 205

Leu Leu Pro Thr Asp Tyr Ile Lys Arg Ile Val Leu Arg Ile Pro Asn
    210                 215                 220

Val Gln Tyr Val Asn Arg Pro Phe Pro Val Ser Glu His Glu Ala Arg
225                 230                 235                 240

His Ser Phe Gln Tyr Val Ala Cys Ala Met Leu Leu Asp Gly Gly Ile
                245                 250                 255

Thr Val Pro Ser Phe His Glu Cys Gln Ile Asn Arg Pro Gln Val Arg
            260                 265                 270

Glu Leu Leu Ser Lys Val Glu Leu Glu Tyr Pro Pro Asp Asn Leu Pro
        275                 280                 285

Ser Phe Asn Ile Leu Tyr Cys Glu Ile Ser Val Thr Leu Lys Asp Gly
    290                 295                 300

Ala Thr Phe Thr Asp Arg Ser Asp Thr Phe Tyr Gly His Trp Arg Lys
305                 310                 315                 320

Pro Leu Ser Gln Glu Asp Leu Glu Glu Lys Phe Arg Ala Asn Ala Ser
                325                 330                 335

Lys Met Leu Ser Trp Asp Thr Val Glu Ser Leu Ile Lys Ile Val Lys
            340                 345                 350
```

```
Asn Leu Glu Asp Leu Glu Asp Cys Ser Val Leu Thr Thr Leu Leu Lys
        355                 360                 365

Gly Pro Ser Pro Pro Glu Val Ala Ser Asn Ser Pro Ala Cys Asn Asn
        370                 375                 380

Ser Ile Thr Asn Leu Ser
385                 390

<210> SEQ ID NO 5
<211> LENGTH: 652
<212> TYPE: DNA
<213> ORGANISM: Homo sapiens
<220> FEATURE:
<221> NAME/KEY: CDS
<222> LOCATION: (56)..(307)

<400> SEQUENCE: 5
ggcaccaggc gcaccgcccg gcgtccagat ttggcaattc ttcgctgaag tcatc atg      58
                                                               Met
                                                                 1 agc ttt ttc caa ctc ctg atg aaa agg aag gaa ctc att ccc ttg gtg     106
Ser Phe Phe Gln Leu Leu Met Lys Arg Lys Glu Leu Ile Pro Leu Val
          5                  10                  15 gtg ttc atg act gtg gcg gcg ggt gga gcc tca tct ttc gct gtg tat     154
Val Phe Met Thr Val Ala Ala Gly Gly Ala Ser Ser Phe Ala Val Tyr
         20                  25                  30 tct ctt tgg aaa acc gat gtg atc ctt gat cga aaa aaa aat cca gaa     202
Ser Leu Trp Lys Thr Asp Val Ile Leu Asp Arg Lys Lys Asn Pro Glu
     35                  40                  45 cct tgg gaa act gtg gac cct act gta cct caa aag ctt ata aca atc     250
Pro Trp Glu Thr Val Asp Pro Thr Val Pro Gln Lys Leu Ile Thr Ile
 50                  55                  60                  65 aac caa caa tgg aaa ccc att gaa gag ttg caa aat gtc caa agg gtg     298
Asn Gln Gln Trp Lys Pro Ile Glu Glu Leu Gln Asn Val Gln Arg Val
                 70                  75                  80 acc aaa tgacgagccc tcgcctcttt cttctgaaga gtactctata aatctagtgg     354
Thr Lys aaacatttct gcacaaacta gattctggac accagtgtgc ggaaatgctt ctgctacatt     414
tttagggttt gtctacattt tttgggctct ggataaggaa ttaaaggagt gcagcaataa     474
ctgcactgtc taaagtttg tgcttatttt cttgtaaatt tgaatattgc atattgaaat     534
ttttgtttat gatctatgaa tgttttctt aaaatttaca aagctttgta aattagattt     594
tctttaataa aatgccattt gtgcaagatt tctcaaagaa aaaaaaaaa aaaaaaaa       652

<210> SEQ ID NO 6
<211> LENGTH: 83
<212> TYPE: PRT
<213> ORGANISM: Homo sapiens

<400> SEQUENCE: 6

Met Ser Phe Phe Gln Leu Leu Met Lys Arg Lys Glu Leu Ile Pro Leu
  1               5                  10                  15

Val Val Phe Met Thr Val Ala Ala Gly Gly Ala Ser Ser Phe Ala Val
             20                  25                  30

Tyr Ser Leu Trp Lys Thr Asp Val Ile Leu Asp Arg Lys Lys Asn Pro
         35                  40                  45

Glu Pro Trp Glu Thr Val Asp Pro Thr Val Pro Gln Lys Leu Ile Thr
     50                  55                  60

Ile Asn Gln Gln Trp Lys Pro Ile Glu Glu Leu Gln Asn Val Gln Arg
 65                  70                  75                  80
```

Val Thr Lys

```
<210> SEQ ID NO 7
<211> LENGTH: 34
<212> TYPE: DNA
<213> ORGANISM: Artificial Sequence
<220> FEATURE:
<223> OTHER INFORMATION: Description of Artificial Sequence: NLG-2
      forward primer

<400> SEQUENCE: 7
cacggatcca ttcttcgctg aagtcatcat gagc                              34

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: NLG-2
      reverse primer

<400> SEQUENCE: 8
gtggaattct ttggtcaccc tttggacatt ttgc                              34

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: NLG-1-1
      forward primer

<400> SEQUENCE: 9
cacggatcct tctttacaac gaaatgatgc tcaag                             35

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: NLG-1-1
      reverse primer

<400> SEQUENCE: 10
gtggaattcg gagagatttg tgatagaatt attacatgc                         39
```